United States Patent
Xie et al.

(10) Patent No.: US 8,377,277 B2
(45) Date of Patent: Feb. 19, 2013

(54) SYSTEM AND METHOD FOR PERFORMING MICROFLUIDIC MANIPULATION

(75) Inventors: Jun Xie, Niskayuna, NY (US); Wei-Cheng Tian, Clifton Park, NY (US); Shashi Thutupalli, Bangalore (IN); Li Zhu, Clifton Park, NY (US); Anthony John Murray, Lebanon, NJ (US); Erin Jean Finehout, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 943 days.

(21) Appl. No.: 12/255,962

(22) Filed: Oct. 22, 2008

(65) Prior Publication Data
US 2010/0096267 A1    Apr. 22, 2010

(51) Int. Cl.
 *B01D 57/02* (2006.01)
(52) U.S. Cl. .................. 204/453; 204/604
(58) Field of Classification Search .......... 422/502–508; 204/403.01–403.15, 450–462, 547–550, 204/600–610, 643–645; 205/777.5, 778, 205/779, 792
See application file for complete search history.

(56) References Cited

U.S. PATENT DOCUMENTS

| | | | |
|---|---|---|---|
| 5,466,351 A * | 11/1995 | Rampal et al. ................ | 204/452 |
| 6,013,168 A | 1/2000 | Arai | |
| 6,454,945 B1 | 9/2002 | Weigl et al. | |
| 7,740,748 B2 * | 6/2010 | Tian et al. .................... | 204/453 |
| 2002/0005354 A1 * | 1/2002 | Spence et al. ................ | 204/450 |
| 2002/0033337 A1 * | 3/2002 | Ausserer et al. .............. | 204/453 |
| 2002/0144907 A1 | 10/2002 | Yamamoto | |
| 2002/0168780 A1 | 11/2002 | Liu et al. | |
| 2004/0009517 A1 * | 1/2004 | Ramsey ......................... | 435/6 |
| 2005/0109621 A1 | 5/2005 | Hauser et al. | |
| 2006/0042948 A1 | 3/2006 | Santiago et al. | |
| 2006/0102482 A1 * | 5/2006 | Auerswald et al. ........... | 204/547 |
| 2006/0147344 A1 | 7/2006 | Ahn et al. | |
| 2006/0169587 A1 | 8/2006 | Lopez et al. | |
| 2007/0039822 A1 | 2/2007 | Henry et al. | |
| 2007/0039823 A1 * | 2/2007 | Bek et al. ...................... | 204/451 |

FOREIGN PATENT DOCUMENTS

| | | |
|---|---|---|
| WO | WO9604547 | 2/1996 |
| WO | WO9924828 | 5/1999 |

OTHER PUBLICATIONS

Beebe, "NMR, Capillary Electrophoresis on a Chip", Oct. 8, 1998, pp. 1-3.
Hammond, "Microchip-based Capillary Electrophoresis: Sequencing and Beyond", Mar. 19, 2001, pp. 1-3.

* cited by examiner

*Primary Examiner* — Kaj K Olsen
*Assistant Examiner* — Susan D Leong
(74) *Attorney, Agent, or Firm* — Jenifer E. Haeckl

(57) ABSTRACT

Electrophoresis systems and methods comprise an electrophoresis device, wherein the electrophoresis comprises a loading channel, a separation channel, and an injection channel. The loading channel is in fluid communication with a first and second sample port. The separation channel is connected to the loading channel to form a first intersection, and an injection channel connected to the separation channel to form a second intersection and in fluid communication with a first reservoir, and wherein the separation channel is in fluid communication with a second reservoir. The electrophoresis system further comprises two electrodes coupled to the first sample port and the first reservoir, and the first sample port and the second reservoir, respectively, that are adapted to move the sample into the loading channel towards the first reservoir and form a sample plug in the separation channel, and to further move the sample plug into the separation channel towards the second reservoir.

5 Claims, 4 Drawing Sheets

SYSTEM AND METHOD FOR PERFORMING MICROFLUIDIC MANIPULATION

BACKGROUND

This invention relates generally to an electrophoresis system and a method for performing microfluidic manipulation. More particularly, this invention relates to a microfluidic chip and a method for electrophoretic separation.

Electrophoresis techniques are widely used in chemical and biology fields, such as DNA sequencing, protein analysis and genetic mapping. The term electrophoresis refers to a process in which charged molecules are separated in a given separation medium, such as an electrolyte solution under influence of an electric filed. The charged molecules migrate through the separation medium and separate into distinct bands due to different electrophoretic mobilities.

A variety of commercial electrophoresis apparatus have been available for analysis of a sample. One such type of the electrophoresis apparatus is a capillary electrophoresis apparatus. The capillary electrophoresis can be considered as one of the latest and most rapidly expanding techniques in analytical chemistry. It refers to a family of related analytical techniques that uses electric fields to separate molecules within narrow-bore capillaries (typically 20-100 um internal diameter).

In capillary electrophoresis, the samples may be injected into the separation capillary in advance for subsequent separation. Current practical techniques for sample injection in the capillary include electromigration and siphoning of the sample from a container into one end of the separation capillary. For the siphoning injection technique, the sample reservoir is coupled to an input end of the capillary and is raised above a buffer reservoir that is at an exit end of the capillary for a fixed length of time. The electromigration injection technique is affected by applying an appropriate polarized electrical potential across the capillary for a given duration while the input end of the capillary is in the sample reservoir. For both sample injection techniques, the input end of the analysis capillary tube must be transferred from the sample reservoir to the buffer reservoir to perform separation. Thus, a mechanical manipulation is involved. It is also difficult to maintain consistency in injecting a fixed volume of the sample by either of these techniques, as the sample volume injected are susceptible to changes in sample viscosity, temperature, etc., thereby resulting in relatively poor reproducibility in the injected sample volumes between separation runs. Electromigration additionally suffers from electrophoretic mobility-based bias.

Therefore, there is a need for a new and improved electrophoresis system and method for performing microfluidic manipulation.

BRIEF DESCRIPTION

An electrophoresis system in accordance with one embodiment of the invention is provided. The electrophoresis system comprises an electrophoresis device. The electrophoresis comprises a loading channel, a separation channel, and an injection channel. The loading channel is in fluid communication with a first and second sample port. The separation channel is connected to the loading channel to form a first intersection, and an injection channel connected to the separation channel to form a second intersection and in fluid communication with a first reservoir, and wherein the separation channel is in fluid communication with a second reservoir. The electrophoresis system further comprises electrodes coupled to the first sample port and the first reservoir, and the first sample port and the second reservoir, respectively, that are adapted to move the sample into the loading channel towards the first reservoir and form a sample plug in the separation channel, and to further move the sample plug into the separation channel towards the second reservoir.

An electrophoresis device in accordance with another embodiment of the invention is provided. The electrophoresis comprises a loading channel, a separation channel, and an injection channel. The loading channel is in fluid communication with a first and second sample port. The separation channel is connected to the loading channel to form a first intersection, and an injection channel connected to the separation channel to form a second intersection and in fluid communication with a first reservoir, and wherein the separation channel is in fluid communication with a second reservoir.

A method for controlling the flow of one or more fluids in an electrophoresis device in accordance with one embodiment is provided. The electrophoresis comprises a loading channel, a separation channel, and an injection channel. The loading channel is in fluid communication with a first and second sample port. The separation channel is connected to the loading channel to form a first intersection, and an injection channel connected to the separation channel to form a second intersection and in fluid communication with a first reservoir, and wherein the separation channel is in fluid communication with a second reservoir. Further, the method comprises loading at least one of a buffer solution and a sieving matrix into the separation channel and the injection channel from one or more of the first and second sample ports and the first and second reservoirs, loading a sample into the loading channel from one of the first and second sample ports, applying a first potential electrically coupled to the first sample port and the first reservoir to move the sample into the loading channel towards the first reservoir and form a sample plug in the separation channel, and applying a second potential electrically coupled to the first sample port and the second reservoir to move the sample plug into the separation channel towards the second reservoir.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE DISCLOSURE

Figure 1:
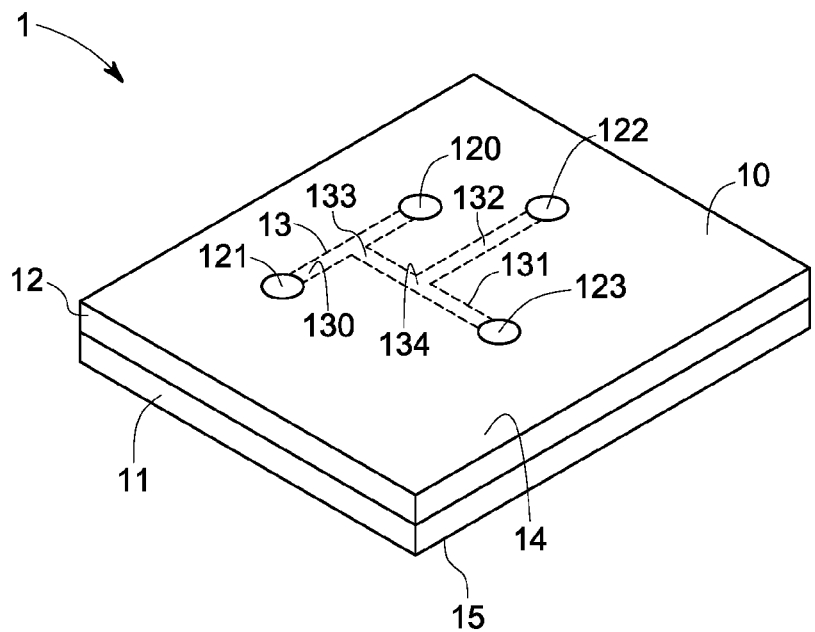
FIG. 1 is a schematic diagram of an electrophoresis system with a channel subsystem in accordance with one embodiment of the invention.

FIG. 1 illustrates a schematic diagram of an electrophoresis system with a channel subsystem in accordance with one embodiment of the invention. As illustrated in FIG. 1, an electrophoresis system 1 comprises an electrophoresis apparatus 10 comprising a substrate 11 and a cover 12 attached on a surface of the substrate 11. In certain embodiments of the invention, the electrophoresis apparatus 10 may be a microfluidic chip. And the substrate 11 and the cover 12 may be made of glass, silicon, or other materials known in the semiconductor arts, or of a suitable polymer material, such as plastic.

Generally, a microfluidic chip, also referred to as a lab-on-a-chip or a microchip, is a miniaturized device for manipulating and analyzing chemical/biological samples in micrometer-sized channels. The microfluidic chip may comprise a chemical/biological microprocessor for use in a variety of processes, such as, not limited to, injection, separation and detection, integrated in a glass, silicon, plastic or other suitable substrate having an area of several square centimeters. It offers faster analysis while using much smaller amount of samples and reagents, usually on a micro-liter scale.

In the illustrated embodiment, the microfluidic chip 10 defines a channel subsystem 13, which is etched, micromachined or otherwise established therein. In one example, the channel subsystem 13 is fabricated by techniques from semiconductor manufacture, such as photolithography etc. The channel subsystem 13 comprises a loading channel 130, a separation channel 131 and an injection channel 132 each disposing in the substrate 11. The separation channel 131 is in fluid communication with the loading channel 130 at one end thereof to form a first intersection 133. The injection channel 132 is in fluid communication with the separation channel 131 perpendicularly at one end thereof to form a second intersection 134.

In one exemplary embodiment, a distance between the first and second intersections 133 and 134 is small, such as 50-200 μm. A width of the loading channel 130 may larger than the widths of the injection and separation channels 131-132. In one example, the width of the loading channel may be about or larger than 500 μm, and the widths of the injection and separation channels 131-132 may be about 50-200 μm. In one or more embodiments, the injection channel 132 may not be perpendicular to the separation channel 131.

Additionally, the channel subsystem 13 comprises a first sample port 120, a second sample port 121, a first reservoir 122 and a second reservoir 123 each passing through the cover 12. In this example, the first sample port 120 and the second sample port 121 communicate with two opposite ends of the loading channel 130, respectively. The first reservoir 122 is in fluid communication with the other end of the injection channel 132 generally located at an end that is opposite to the end that is in fluid communication with the separation channel 131. The second reservoir 123 is in fluid communication with another end of the separation channel 131 opposite to the one end thereof. In one exemplary embodiment, the first intersection 133 is located between the first and second sample ports 120 and 121, and is adjacent, or otherwise in close proximity, to the first sample port 120.

Figure 4:
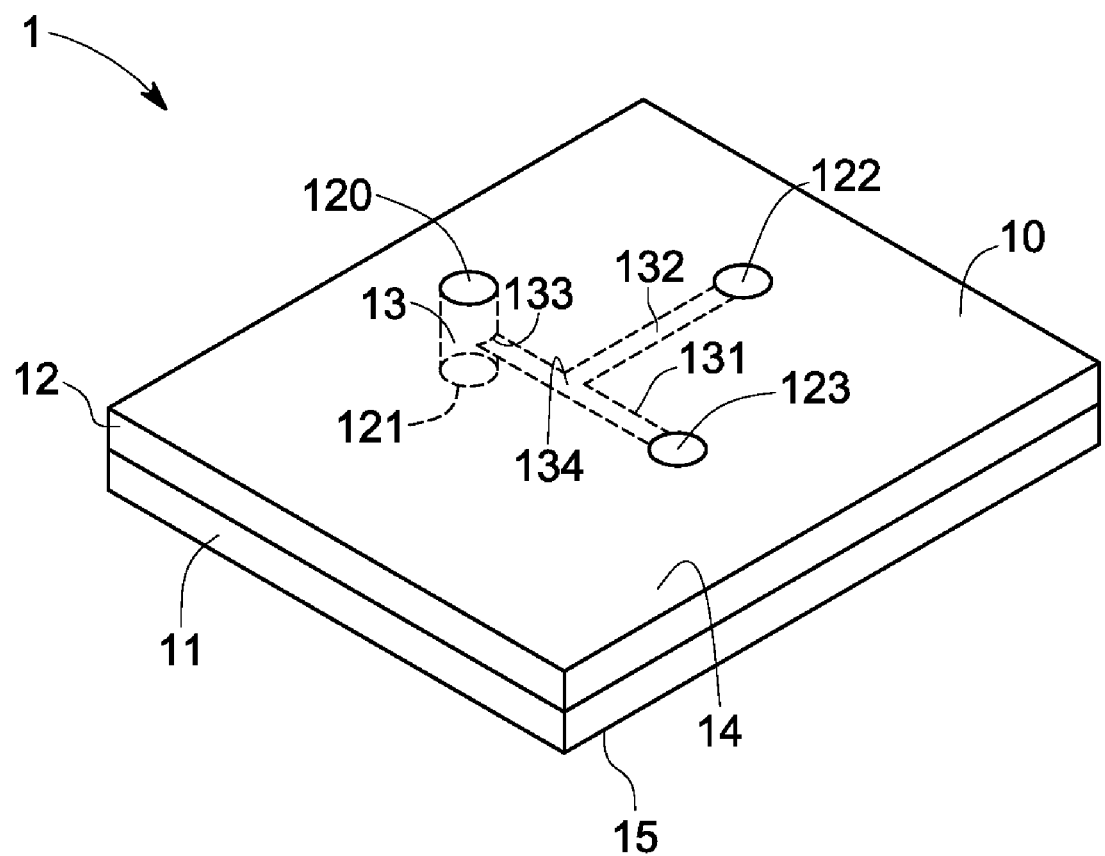
FIG. 4 is a schematic diagram of the channel subsystem of the electrophoresis system in accordance with another embodiment of the invention.

Further, as illustrated in FIG. 4, the loading channel 130 may pass through the substrate 11 and the cover 12 vertically. The first sample port 120 and the second sample port 121 may locate on an upper surface 14 (shown in FIG. 1) of the cover 12 and a lower surface 15 (shown in FIG. 1) of the substrate 11, respectively. Thus, this configuration may minimize a dead/swept volume of a sample, and reduce a pressure drop on the loading channel 130.

In one or more embodiments of the invention, the loading channel 130 is used for loading a sample from the first sample port 120 or the second sample port 121 using various pressure driven methods. In one example, when using a positive pressure to push the sample into the loading channel 130, the second sample port 121 may be used as a sample inlet on which the positive pressure is exerted. When using a negative pressure to draw the sample into the loading channel 130, the first sample port 120 can be used as the sample inlet, and the negative pressure is exerted on the second sample port 121. Thus, reducing effect of the injection pressure on the separation channel 131 and the injection channel 132. Accordingly, the first sample port 120 or the second sample port 121 may be used as a sample outlet.

The separation channel 131 between the first and second intersections 133-134 and the injection channel 132 are used for receiving a part of the sample from the loading channel 130. Additionally, the separation channel 131 behind the second intersection 134 can receive the sample in the separation channel 131 between the first and second intersections 133 and 134 for sample separation. In one example, the sample in the second intersection 134 may not flow in the separation channel 131 behind the second intersection 134.

In one or more embodiments of the invention, the first reservoir 122 may be used as a waste sample reservoir to accommodate the waste sample from the injection channel 132. The second reservoir 123 may be used as a separation waste reservoir to accommodate the separation waste from the separation channel 131. At least one of the first and second sample ports 120-121 and the first and second reservoirs 122-123 may also be used as a buffer reservoir and/or a sieving matrix reservoir for injecting a buffer solution and/or a sieving matrix into the channels. In one or more embodiments of the invention, the buffer solution may comprise sodium dodecyl sulfate and the sieving matrix may comprise polyethylene oxide.

Figure 2A:
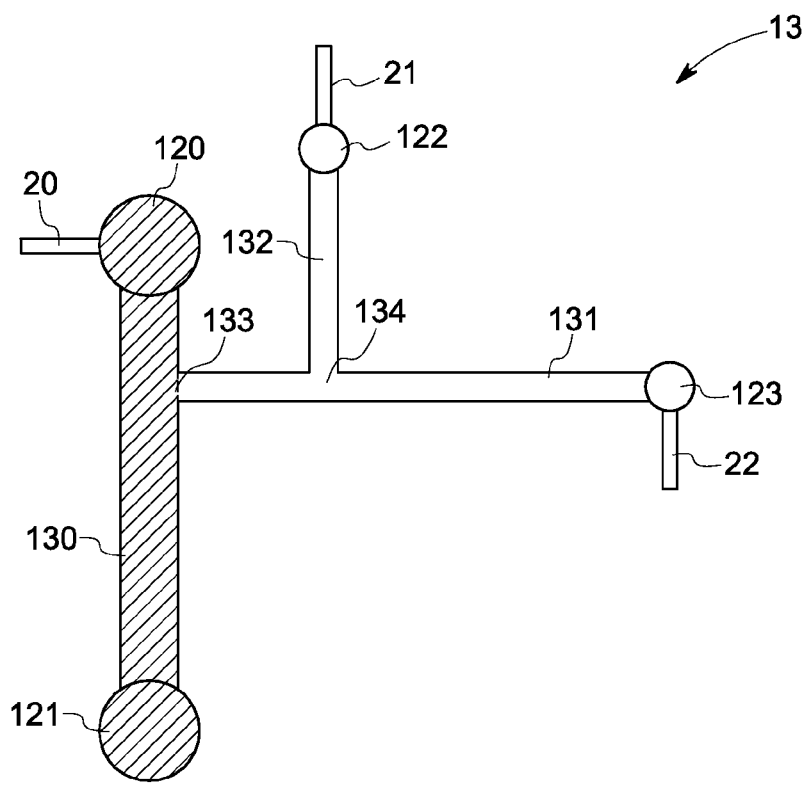
FIGS. 2(a)-2(d) are schematic flow diagrams of steps for injecting and separating a sample in accordance with one embodiment of the invention.

FIGS. 2(a)-2(d) are schematic flow diagrams of an example embodiment of the steps for injecting and separating a sample. As illustrated in FIG. 2(a), the electrophoresis system 1 further comprises a first electrode 20 disposed in the first sample port 120, a second electrode 21 disposed in the first reservoir 122 and a third electrode 22 disposed in the second reservoir 123. In one or more embodiments of the invention, the electrodes may be disposed detachably in the respective sample ports and reservoirs. Alternatively, the electrodes may be integrated into the microfluidic chip 10 (shown in FIG. 1).

In the illustrated embodiment, during operation, at least one of a first buffer solution and a first sieving matrix may be injected into all the channels in advance from at least one of the first sample port 120, the second sample port 121, the first reservoir 122, and the second reservoir 123. In one embodiment, at least one of the first buffer solution and the first sieving matrix may be injected into the separation channel 131 and the injection channel 132 in advance from at least one of first reservoir 122 and the second reservoir 123. In certain embodiments, when injecting both the first buffer solution and the first sieving matrix, the sieving matrix may just be injected into the separation channel 131 behind the second intersection 134 from the second reservoir 123.

Next, referring to FIG. 2(a), in this example, the sample is pressure loaded into the loading channel 130 from the first sample port 120 or the second sample port 121 to replace the first buffer solution and/or the first sieving matrix in the loading channel 130. In one embodiment, the first buffer solution or the first sieving matrix may be employed to pretreat the sample before the sample is loaded in the loading channel 130.

Figure 2B:
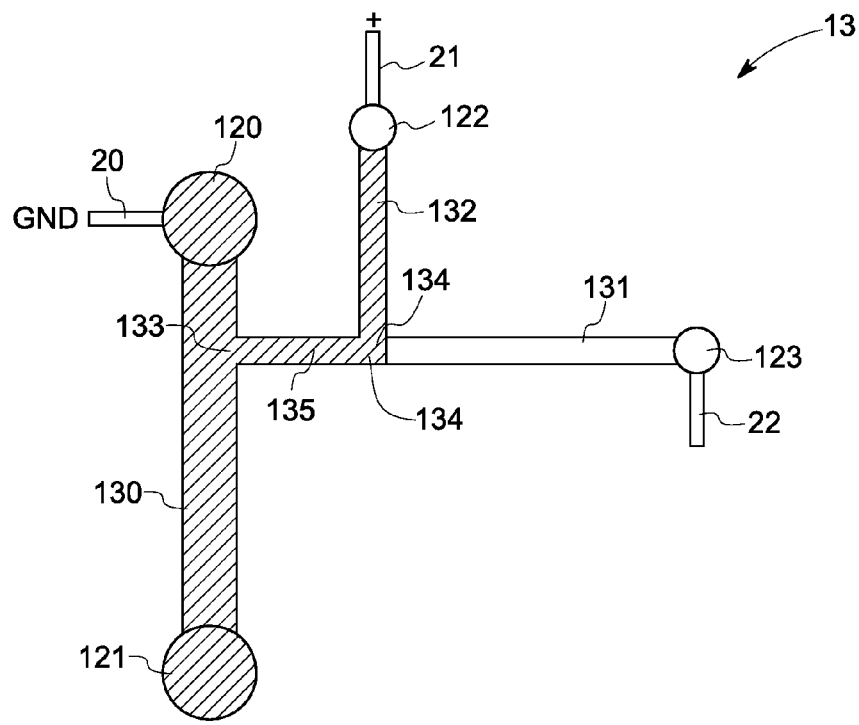

Referring to FIG. 2(b), a first potential is applied across the first electrode 20 and the second electrode 21 to form a first flow pattern for moving the sample in the loading channel 130 towards the first reservoir 122 and to flow into the injection channel 132 and the separation channel 131 between first and second intersections 133 and 134, and form a sample plug 135 in the separation channel 131 by electroosmotic flow. In the illustrated embodiment, the first electrode 20 is grounded (indicated by GND) and the second electrode 21 is applied with a first positive potential. To ensure that the composition of the sample in the sample plug 135 reflects the actual sample composition in the loading channel 130, the electrical field across the first electrode 20 and the second electrode 21 must be maintained for a sufficient period of time.

Figure 2C:
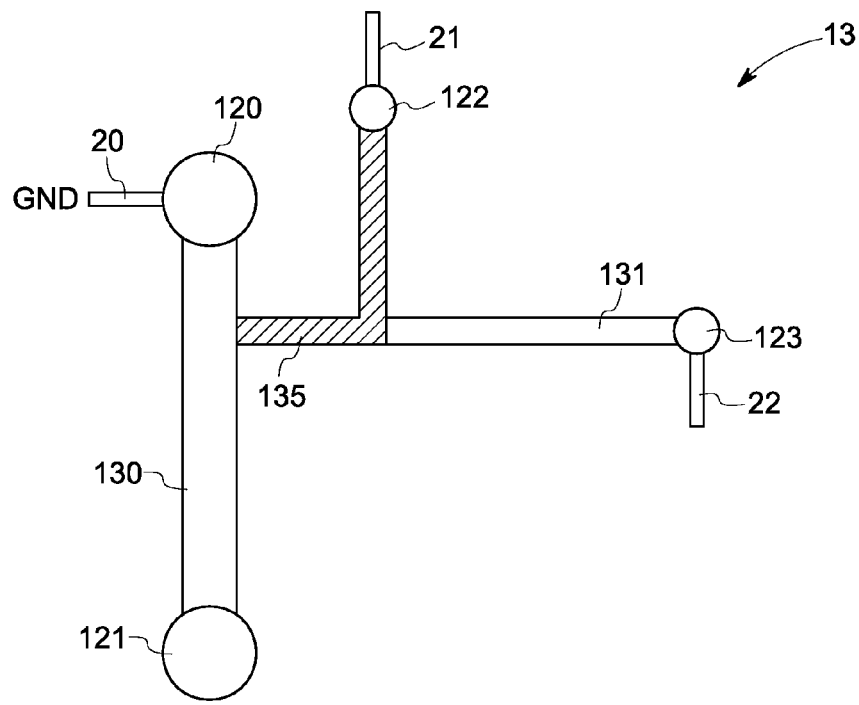

Following this, in one example, as illustrated in FIG. 2(c), the potential may be shut off, and a second buffer solution or a second sieving matrix same as or similar to the first buffer solution or first sieving matrix, respectively, may be injected into the loading channel 130 to rinse away the sample therein.

Figure 2D:
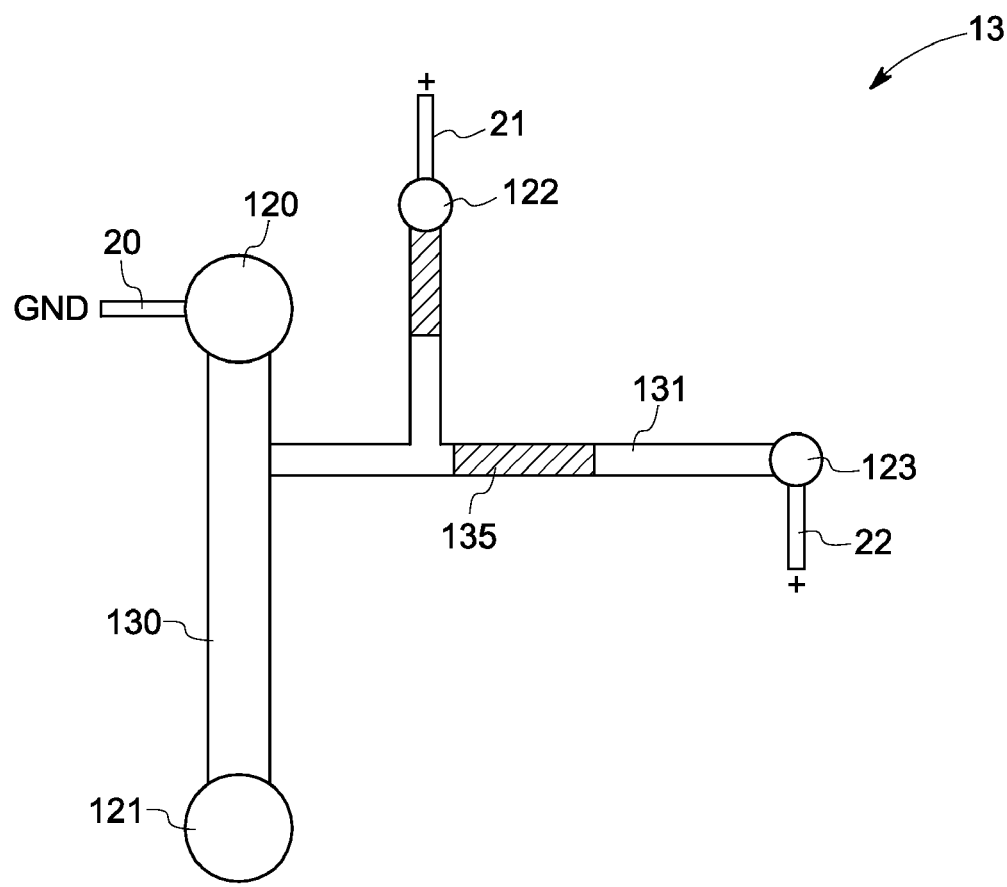

Subsequently, as illustrated in FIG. 2(d), a second potential is applied on the third electrode 22 and the first electrode 20 to form a second flow pattern for pulling the sample plug 135 towards the third reservoir 123 to be separated in the separation channel 131. In one embodiment, the first electrode 20 is grounded and the third electrode 22 is applied with a second positive potential. In other embodiments, the first potential applied to the first electrode 20 and the second electrode 21 may also be resumed to pull the sample in the injection channel 132 into the first reservoir 122 while the second potential is applied. That is, the first potential may be employed simultaneously or overlapped with applying of the second potential.

In one or more embodiments, the step for shutting off the first potential and rinsing away the sample may not be employed. Thus, the third electrode 22 can be directly applied with the second potential to pull the sample plug 135 for separation. In some embodiments of the invention, the first electrode 20 may also be applied with a negative potential and the second and third electrodes 21-22 may be grounded. In certain embodiments, the sample plug 135 may not include the sample in the second intersection 134 to ensure an accurate amount of the sample for separation.

Figure 3:
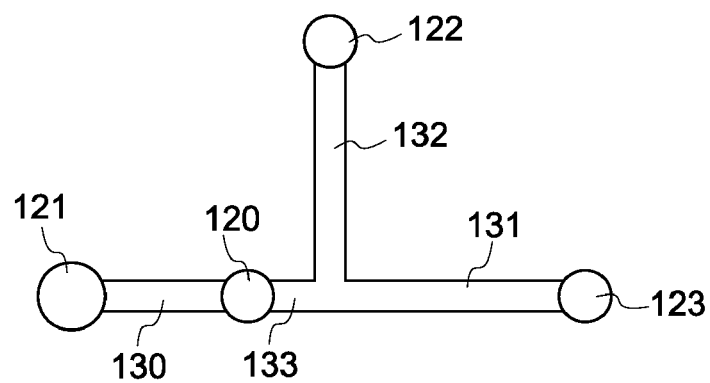
FIG. 3 is a schematic diagram of the channel subsystem in accordance with another embodiment of the invention.

FIG. 3 illustrates a schematic diagram of the channel subsystem of the electrophoresis system in accordance with another embodiment of the invention. The embodiment in FIG. 3 is similar to that in FIG. 1, and the same numerals therein may denote the same elements. The difference between FIGS. 1 and 3 is that the first intersection 133 in FIG. 3 is in fluid communication with the first sample port 120 directly, and is not located between the first and second sample ports 120-121.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for controlling the flow of one or more fluids in an electrophoresis device, comprising the steps of:
   providing an electrophoresis device comprising:
      a loading channel in fluid communication with a first and second sample port,
      a separation channel connected to the loading channel to form a first intersection,
      an injection channel connected to the separation channel to form a second intersection and in fluid communication with a first reservoir, wherein the separation channel is in fluid communication with a second reservoir, wherein the injection channel is configured to receive and deliver a part of the sample from the loading channel to the first reservoir; and
   loading at least one of a buffer solution and a sieving matrix into the separation channel and the injection channel from one or more of the first and second sample ports and the first and second reservoirs;
   loading a sample into the loading channel from one of the first and second sample ports;
   applying a first potential electrically coupled to the first sample port and the first reservoir to move the sample into the loading channel towards the first reservoir and form a sample plug in the separation channel; and
   applying a second potential electrically coupled to the first sample port and the second reservoir to move the sample plug into the separation channel towards the second reservoir.

2. The method of claim 1, further comprising a step of shutting off the first potential and rinsing away the sample in the loading channel after the step of forming the sample plug in the separation channel.

3. The method of claim 2, wherein the step of applying the first potential is overlapped with the step of applying the second potential.

4. The method of claim 1, wherein the electrophoresis device comprises a microfluidic chip.

5. The method of claim 1, further comprising a step of disposing a first, a second, and a third electrodes coupled to the first sample port, the first reservoir, and the second reservoir, respectively after the step of loading the sample into the loading channel.

* * * * *